United States Patent
Dolatkhani et al.

(10) Patent No.: US 9,393,346 B2
(45) Date of Patent: Jul. 19, 2016

(54) POLYMER CEMENTS USED FOR FIXING PROSTHESES, FOR BONE REPAIR AND FOR VERTEBROPLASTY, AND OBTAINED FROM LIQUID SINGLE-PHASE FORMULATIONS

(71) Applicant: POLYMEREXPERT SA, Pessac (FR)

(72) Inventors: Marc Dolatkhani, Cestas (FR); Christophe Hupin, Salles (FR)

(73) Assignee: POLYMEREXPERT SA, Pessac (FR)

( * ) Notice: Subject to any disclaimer, the term of this patent is extended or adjusted under 35 U.S.C. 154(b) by 0 days.

(21) Appl. No.: 14/363,950

(22) PCT Filed: Dec. 7, 2012

(86) PCT No.: PCT/FR2012/052847
§ 371 (c)(1),
(2) Date: Jun. 9, 2014

(87) PCT Pub. No.: WO2013/083935
PCT Pub. Date: Jun. 13, 2013

(65) Prior Publication Data
US 2014/0357753 A1    Dec. 4, 2014

(30) Foreign Application Priority Data
Dec. 9, 2011 (FR) ..................... 11 61395

(51) Int. Cl.
| A61K 6/083 | (2006.01) |
| A61L 27/16 | (2006.01) |
| A61L 24/06 | (2006.01) |
| A61B 17/88 | (2006.01) |
| C08L 33/12 | (2006.01) |
| C08L 53/00 | (2006.01) |

(52) U.S. Cl.
CPC .............. *A61L 24/06* (2013.01); *A61B 17/8805* (2013.01); *A61B 17/8833* (2013.01); *A61L 27/16* (2013.01); *C08L 33/12* (2013.01); *C08L 53/00* (2013.01); *A61B 2017/8838* (2013.01); *A61L 2430/02* (2013.01); *C08L 2203/02* (2013.01)

(58) Field of Classification Search
USPC ...................................... 523/117, 116; 606/94
See application file for complete search history.

(56) References Cited

U.S. PATENT DOCUMENTS

| 6,583,394 B2 * | 6/2003 | Araya et al. ................... 219/685 |
| 7,186,761 B2 * | 3/2007 | Soffiati et al. ................. 523/117 |
| 8,415,407 B2 * | 4/2013 | Beyar et al. ................... 523/117 |
| 2007/0027230 A1 | 2/2007 | Beyar |
| 2010/0228358 A1 | 9/2010 | Leonard |
| 2011/0313078 A1 * | 12/2011 | Vogt et al. ..................... 523/116 |

FOREIGN PATENT DOCUMENTS

| CA | 2284925 A1 * | 6/1998 |
| EP | 0747114 * | 12/1996 |
| WO | 2010/005442 A1 | 1/2010 |
| WO | WO 2010/077606 * | 7/2010 |
| WO | 2010/115138 A2 | 10/2010 |
| WO | 2011/004355 A2 | 1/2011 |

* cited by examiner

*Primary Examiner* — Tae H Yoon
(74) *Attorney, Agent, or Firm* — Lucas & Mercanti, LLP

(57) ABSTRACT

The invention relates to a process for preparing cements used for reparative or reconstructive bone surgery, in particular for fixing prostheses, for bone repair and for vertebroplasty, and obtained from liquid single-phase formulations. It also relates to the cements prepared from these single-phase formulations and to a device for injecting them.

18 Claims, 2 Drawing Sheets

POLYMER CEMENTS USED FOR FIXING PROSTHESES, FOR BONE REPAIR AND FOR VERTEBROPLASTY, AND OBTAINED FROM LIQUID SINGLE-PHASE FORMULATIONS

CROSS-REFERENCE TO RELATED APPLICATIONS

This application is a 371 of PCT/FR2012/052847 filed Dec. 7, 2012, which in turn claims the priority of FR 1161395 filed Dec. 9, 2011, the priority of both applications is hereby claimed and both applications are incorporated by reference herein.

SUMMARY OF THE INVENTION

The invention relates to a method for preparing polymer cements for reparative surgery or for bone reconstruction, in particular for fixation of prostheses, for bone repair or for vertebroplasty, starting from liquid single-phase formulations, as well as the cements prepared from these single-phase formulations. It also relates to a device for injecting these formulations at the treatment site, as well as a method of use by activation/injection of said liquid single-phase preparations.

BACKGROUND OF THE INVENTION

Polymer cements are widely used in reconstructive surgery for the fixation of prostheses, for bone repair and for vertebroplasty. The first cements for bone repair and filling appeared in the 1960s following the research of J. Charley (J. Bone Joint Surge, 1960, 42B:28), on the use of thermosetting pastes based on acrylic monomers, more particularly based on methyl methacrylate (MMA), for fixation of a prosthesis on a femur.

This technique was soon recognized as the standard procedure for the fixation of prostheses. Improvements in the formulation of these cements were made later, in particular by adding radio-opacifying fillers allowing visualization of the cement during and after the procedure, or else by adding antibiotics that are gradually released by the cement, thus reducing the risks of infection.

At present there are about thirty commercial brands of cement formulations for the fixation of prostheses and bone repair approved by the Agence Française de Sécurité Sanitaire des Produits de Santé [French agency for the safety of health products] and the Food and Drug Administration (Lewis G., J Biomed Mater Res Appl. Biomater. 2008, 84B: 301).

Two main types of formulations for acrylic cements can be distinguished: formulations for high-viscosity cements, for which the surgeon mixes and moulds the paste by hand, and formulations for cements with low or medium viscosity intended to be injected via a syringe or a trocar, and which are used in particular in bone filling and vertebroplasty (Lewis G., J. Biomed. Mater Res B, 2006, Appl Biomater, 763: 456-468). All the formulations for polymer cements are based on two-phase or multiphase preparations, which the practitioner must mix manually just before use. The term "phase" applies here to any liquid or solid formulation contained and stored separately in a reservoir, such as a liquid solution, a liquid or solid mixture, either homogeneous or of homogeneous appearance at the macroscopic level (stable suspension, mixture of powders, etc.).

Thus, by "two-phase or multiphase formulation" or "two-phase or multiphase preparation" is meant that the different components involved in the preparation of the polymer cements, namely monomers, polymers, radio-opacifying agent, initiator, activator as well as any other additive, are distributed in several phases stored in separate reservoirs (at least two), the phases contained in the different reservoirs being mixed to initiate setting of the cement, just before or during the injection operation. The purpose of these two-phase or multiphase formulations is to avoid the monomers being in contact with the initiator or, even worse, the monomers being in contact simultaneously with the initiator and the activator, thus preventing initiation of the polymerization reaction and rapid, inadmissible caking of the formulations.

A review of this field shows that, still today, nearly all the commercial cements are in the form of a solid, powder phase and a liquid phase, to be mixed (the main ones being Osteopal-V®, Osteo-Firm®, Vertebroplastic®, Simplex®, Cranioplastic®, Palaces®, CMV®, KyphX HV-R®).

The solid phase mainly contains beads of poly(methyl methacrylate) (PMMA) or PMMA copolymers (co-PMMA), an initiator of radical polymerization, generally benzoyl peroxide (BPO), and a radio-opacifying filler, such as barium sulphate ($BaSO_4$) or zirconium dioxide ($ZrO_2$). The liquid phase consists of monomer(s), such as for example methyl methacrylate (MMA), optionally mixed with co-monomers, and a radical activator, generally N,N-dimethyl-p-toluidine (DMPT) when BPO is used in the solid phase (McGraw J K at al. 2003, J Vasc Intery Radiol; 14: S311-5).

In these two-phase formulations, the monomers are therefore neither in contact with the initiator, nor with the initiator/activator combination during the storage phase, the mixture being made at the moment of application.

These two-phase formulations, constituted by a liquid phase and a solid phase, which are mixed together to produce the cement just before it is injected, are called "standard formulation" in the present document.

These cements, originally designed for the fixation of prostheses, were applied in vertebroplasty in 1985 (Galibert P et al., 1987, Neurochirurgie, 33: 166). The principle relates to introducing the cement preparation into a damaged vertebra; on hardening in situ, it will constitute a mechanical reinforcement by filling the cavity. The indications for this procedure are, in particular, vertebral angiomas, spinal metastases leading to vertebral fractures, and osteoporotic collapse, which in particular affects women and elderly men.

With the ageing of the population, vertebroplasty is undergoing rapid growth. The number of procedures is estimated at 2 million per year, for a market worth 3 billion dollars. Just in the United States and Europe, 700 000 and 450 000 clinical cases of vertebral fracture are detected per year, respectively.

The surgical technique proper consists of injecting percutaneously, under radiological control, a polymer cement of low or medium viscosity into a pathological vertebra to obtain consolidation of said vertebra. For this procedure, the practitioner generally operates under local anaesthesia, perforating the vertebral body using a trocar, and follows the procedure using radiography. Once the trocar is ideally placed, a radio-opaque acrylic cement, of the same type as those used for operations involving the hip or the knees, is prepared by mixing the various components, and is then injected so as to fill the vertebral body. On hardening by polymerization, the cement will thus reinforce the vertebra.

With most of the commercial cements, to be able to perform vertebroplasty, the practitioner must, in a first manual step, mix the various formulations containing the components of the cement with vigorous stirring, until the cement begins to set, characterized by a rapid increase in its viscosity and its temperature. This preliminary step, on the one hand, exposes practitioners to the toxic vapours of the monomer and of the activator (DMPT) and on the other hand constitutes, owing to its manual character, a known cause of non-uniformity in the properties of the cements obtained, in particular because of inclusion of air bubbles formed under stirring. These bubbles will cause, after polymerization, the appearance of pores, varying in size, and will lead to brittle zones in the material.

The duration of this initial polymerization step depends on the composition of the formulations, on the ambient temperature but also on the manner of stirring and of mixing the different phases, which vary with each technician. This preliminary step, carried out in the presence of the oxygen of the air, may also cause a varying degree of partial deactivation of the radicals initiating the polymerization reaction. The variability associated with this step of manual mixing under air has been reduced by using the method that consists of centrifugation/mechanical mixing of the powder/liquid mixture under moderate vacuum, but this technique requires special equipment in the operating theatre (Wixson, P. I. et al. J. of Arthroplasty, 1987, Vol, 2, Issue 2, 141-149).

The end of this initial step is defined empirically as being the moment when the cement no longer sticks to the practitioner's gloves. The "working" time during which the cement is then usable, i.e. introduced into the syringe and then injected via the trocar, is limited to a few minutes (typically 8 to 15 minutes). A cement for which setting is too advanced risks blocking the trocar, whereas a cement that is too fluid (containing a high proportion of toxic monomer, still unpolymerized) presents the risk of flowing out of the vertebra, causing significant post-operative complications (venous compression, peridural loss, arterial hypotension, etc.). These risks can be reduced by passing a balloon into the vertebra beforehand, this balloon then being inflated in situ to straighten the vertebra and create a more impervious cavity into which the cement is introduced. This is then called kyphoplasty, but this makes the procedure more complex, more difficult and more expensive.

Other approaches have been proposed to improve the procedures and reduce the surgical risks.

Patent application WO2010/005442 relates to preparations of "multi-solution" or else multiphase liquid/liquid cements constituted by two liquid formulations (phases). The liquid formulations described are constituted by solutions (or more precisely suspensions, in many cases), based on monomer (MMA) containing polymer (PMMA) chains in various forms (linear, crosslinked particles, combs), and a radio-opacifying agent; one of the formulations containing in addition the initiator (BPO) and the other the activator (DMPT). These two formulations are placed each in a chamber of a two-chamber injector, installed at the outlet of a mixer in which the two liquid formulations are brought into contact and mixed at the moment of the injection operation. The starting of polymerization of the MMA that follows results from the combined action of BPO and of DMPT on the monomer(s).

A major drawback of this method is the reduced stability of the solution of MMA containing BPO, the decomposition of which into initiator radicals takes place slowly but continuously, even at temperatures of 10° C., or even at lower temperatures, as reported by Sivaram, S. et al., Polymer Bulletin, 1980, 3, 1-2, 27-35. This limits the storage and usage over time of these liquid formulations, the viscosity of which increases even when they are stored in a refrigerator (4° C.). Moreover, it is well known that injection of two phases having different viscosities using a two-compartment syringe is difficult to control and presents risks of inhomogeneity in the distribution of the components of the two phases during mixing, and this inhomogeneity affects the final properties of the cements.

With the same objective, namely to automate the process and reduce the manual operations, application US 2007/0027230 describes devices for preparing, mixing and injecting cements of high viscosity (typically above 500 Pa·s and that may reach 2000 Pa·s after a period ranging from a few minutes to about ten minutes) into the patient's vertebra. The injection devices described are able to apply very high pressures, making it possible to prepare and introduce cements of high viscosity to the vertebra to be treated. Two-phase or single-phase compositions for high-viscosity cements having various hardening rates and hardness characteristics are claimed.

With respect to cements constituted on the basis of two separate phases, one liquid containing monomer, activator and various additives, the other solid containing polymer, initiator and other additives, these correspond to "standard" formulations as they lead to high-viscosity cements.

The single-phase formulations described in application US 2007/0027230 are constituted by a single phase containing one or more polymers without a monomer component. The corresponding "high viscosity" cements do not use any polymerization step and their "hardening" is based solely on the change in thermomechanical properties of the polymers with the temperature. These "all polymer" formulations are constituted by a polymer or a mixture of polymers having softening points (Tg) slightly above body temperature. They are injected at a temperature above the softening point using a device allowing high pressures to be applied. These cements with very high viscosity are called "non-hardening".

This strategy, based on the design of "high-pressure" injection devices, which may or may not integrate the steps of preparation/mixing of "high-viscosity" cements, allows the absence, or the use of a reduced quantity, of toxic monomer, which limits the risks inherent in its introduction into the patient's body. This approach also makes it possible to limit or even eliminate the temperature peak that characterizes the polymerization step (Tpeak>80° C. in certain methods), avoiding the risks of necrosis of adjacent tissues. However, this technique requires the application of very high pressures (200 atmospheres, or even higher), which constitutes a considerable risk of damage and/or rupture of the vertebrae or bone to be consolidated, which are in a weakened state.

Another problem, encountered in particular in bone repair and in vertebroplasty, concerns the excessive hardness and low compressibility and flexibility of the existing commercial cements, which may lead to new bone fractures through transmission of mechanical stresses. This is relatively frequent at the level of the repaired vertebra, but also at the level of the adjacent vertebrae, to which the stresses are transferred directly without damping. Thus, Grados at all (Rheumatology 2000; 39: 1410-4) reported, in a mean follow-up of four years, that the relative risk of vertebral fracture in the vicinity of a collapsed vertebra increased from 1.44 to 2.27 after vertebroplasty.

Similarly, Cyteval at al. (AJR 1999; 173: 1685-90) detected new vertebral fractures in 25% of cases at the end of six months after treating fractures. In an attempt to correct this problem, cements were developed having characteristics of hardness and of compressibility appropriate to the properties of the vertebra or any other element to be treated.

Thus, application US2007/0027230 cited above, as well as applications WO2010/115138, WO2011/004355 and US2010/0228358, propose special formulations of cements combining, respectively, either particular polymers, such as modified PMMAs that provide porosity, or particles of hydrophilic crosslinked polymers, or else particles of glass or of ceramics in order to modulate the properties of hardness and of compressibility of the cements. Saving exceptions, these cements are prepared by manual mixing of a liquid phase and a solid phase.

Therefore there are still no completely satisfactory methods for preparing and applying formulations leading to acrylic cements displaying optimum properties for vertebroplasty. In particular, there is no method based on the simple application of single-phase preparations for polymer cements excluding any complex operation of mixing phases together.

BRIEF DESCRIPTION OF THE INVENTION

Innovations such as those provided by the invention make it possible to simplify and control the steps of preparation and injection of polymer cements.

Thus, the invention uses a single-phase formulation based on monomer(s) containing the polymer or polymers or (co)polymer(s) dissolved and/or in suspension, a polymerization activator, and optionally at least one radio-opacifying agent and various other additives.

By "single-phase formulation" is meant that this formulation, which contains several components (in solution or in suspension), is contained in a single reservoir.

"Liquid" means that this formulation may be in the form of solution or suspension having a viscosity such that it can be injected by means of an injection device, for example of the syringe type, usually used in the field of vertebroplasty, without requiring the application of high pressure that might damage the vertebra or bone.

The liquid single-phase formulation according to the invention is stored in the reservoir of a sealed injection device and polymerization is activated during the injection operation by passage over a thin layer or film of the initiator deposited on an element of the device. Besides its ease of application, said formulation, once it has passed over the film of initiator, does not require any particular waiting time before injection into the vertebra or bone, as the polymer film containing the initiator dissolves immediately during passage of the single-phase formulation. This represents a major advantage relative to the two-phase or multiphase methods in which the polymer in the form of solid particles must be mixed with the monomer phase, and then dissolved, which requires a waiting time of variable duration, at the practitioners discretion, before it is injected.

Moreover, the stability over time of the liquid single-phase formulation according to the invention, stored in the absence of the initiator, is also an important advantage relative to liquid/liquid formulations in which one of the phases containing the monomer is in contact with the initiator, which poses a high risk of polymerization.

Compared to the non-hardening single-phase formulations, based on injection, at high temperature and at high pressures, of compositions in the molten state (US 2007/0027230), the formulations according to the invention offer the advantage of utilization at ambient temperature and at pressures that do not present a risk of damaging the vertebrae.

Finally, the invention relates to the use of special (co)polymer systems giving cements having an elastomeric flexible phase dispersed in a more rigid polymer matrix, the cements thus obtained having properties of mechanical strength and of compressibility appropriate to the zone to be consolidated and making it possible to limit the risks of propagation of high stresses and of bone fractures.

The benefits supplied by this novel method for the fixation of prostheses, for bone repair and for vertebroplasty are eagerly awaited by practitioners and will improve the treatment of patients.

The present invention relates to a method for preparing polymer cements for reparative surgery or for bone reconstruction, in particular for the fixation of prostheses, for bone repair and for vertebroplasty, from particular liquid single-phase formulations.

These cements may be used in the fields of reparative surgery or reconstruction, or in cosmetic surgery, in human or veterinary surgery.

The invention also relates to the particular cements obtained by this method, as well as a specific method of activation/injection of these formulations and a dedicated applicator.

The liquid single-phase formulations comprise solutions or suspensions of polymers or of copolymers, of polymerization activator(s), of radio-opacifying agent(s) if necessary, and optionally of additives (antibiotics, inhibitors etc.) in monomers, preferably acrylic monomers.

The injection device, which is also an object of the invention, comprises a single-compartment injector (containing the single-phase formulation) equipped at the outlet with a supporting element, such as for example a static mixer, on which a thin layer or a film containing the polymerization initiator is deposited, or else a needle or a cannula, inside which a thin layer or a film containing the polymerization initiator is deposited. During the injection operation, the liquid single-phase formulation is brought into contact with the initiator by passage over the film containing the initiator, thus leading to its dissolution and bringing the latter into contact with the activator and the monomer(s), which initiates polymerization. A trocar fixed at the end of the static mixer makes it possible to introduce the formulation directly into the bone cavity where the prosthesis is to be fixed or into the bone or vertebra to be consolidated, avoiding any manual mixing, any operation of removing bubbles and any contact of the formulation with the external environment and the risks that are associated with this.

The invention therefore relates to a method of preparing and applying injectable biomedical cements based on the use of single-phase formulations, as well as the particular cements that result therefrom, and the device by which they are injected.

Said method comprises bringing a liquid single-phase formulation, said formulation comprising a liquid phase containing at least one polymer or copolymer in solution or in suspension in at least one monomer, and at least one activator of radical polymerization, into contact with an initiator of radical polymerization deposited in the form of a thin layer or film on a support.

Preferably, said liquid single-phase formulation also contains at least one radio-opacifying agent.

Advantageously, bringing said liquid single-phase formulation into contact with an initiator of radical polymerization deposited in the form of a thin layer or film on a support allows dissolution of said thin layer or film containing the initiator, bringing into contact the initiator and polymerization activator and initiation of polymerization of the monomer or monomers.

In particular, said contacting is carried out by the passage of said liquid single-phase formulation over an element comprising a support, on which a thin layer or film containing an initiator of radical polymerization is deposited.

Thus, the thin layer or film containing the initiator of radical polymerization dissolves during passage of the single-phase formulation and allows rapid dissolution of the initiator of radical polymerization as well as distribution thereof within the liquid single-phase formulation.

Advantageously, bringing said liquid single-phase formulation into contact with an initiator of radical polymerization deposited in the form of a thin layer or film on a support takes place at the moment of the surgical procedure.

Advantageously, said bringing the liquid single-phase formulation into contact with the thin layer or film containing the initiator takes place in an injection device, in which said liquid single-phase formulation is contained in the single reservoir of the injection device (single-compartment injector) equipped at the outlet with an element comprising a support on which a thin layer or film of the polymerization initiator is deposited. During the injection operation, the liquid single-phase formulation is brought into contact with the initiator by passage over the film containing the initiator.

According to an alternative, the method according to the invention comprises a step of prepolymerization of the single-phase formulation in an element of an injection device comprising a support on which a thin layer (or film) containing a polymerization initiator is deposited, carried out by activation of the polymerization initiator by the activator contained in the single-phase formulation. According to the invention, the single-phase formulations may comprise solutions or liquid suspensions of acrylic monomers, containing polymers or copolymers, one or more radio-opacifying agents, one or more activator(s) of radical polymerization and optionally one or more additive(s) (antibiotics, free radical inhibitors, etc.), together constituting the single phase.

Advantageously, the liquid single-phase formulation according to the invention contains at least one acrylic, preferably (meth)acrylic, monomer, one or more polymers or copolymers, at least one activator of radical polymerization, at least one radio-opacifying agent and at least one additive.

Preferably, said formulations are constituted by the solutions or suspensions defined above.

Advantageously, these liquid single-phase formulations have good stability over time, and do not undergo any notable change until the process of polymerization of the monomers that they contain is deliberately started by the practitioner at the moment of the surgical procedure requiring injection of the cement. This means in particular that there should not be any spontaneous polymerization of the monomers within the formulation. This is achieved by preventing any contact between the monomer or monomers present and any radical-generating initiator compound, or by blocking the radicals that might form for example by adding a suitable amount of an inhibitor.

The monomer in liquid form in which the polymers or copolymers are dissolved—or suspended—to form the single-phase formulation may be an acrylic derivative, such as pure methyl methacrylate (MMA) or a mixture of monomers such as MMA with co-monomers of the acrylate or methacrylate type, for example butyl (meth)acrylate (MABu) or any other acrylic or methacrylic monomer for example ethyl (meth)acrylate or 2-ethylhexyl (meth)acrylate or else a non-acrylic monomer having one or more unsaturations liable to polymerize by a radical mechanism.

By adjusting the ratio of the quantity of monomer to the quantity of polymers, it is possible to optimize the viscosity of the formulation to allow injection at pressures posing no risk of damage for the vertebrae or bone.

Preferably, this weight ratio is between 20 and 75%.

The incorporation of co-monomers in the forming chains of PMMA makes it possible to modulate the physical properties of the polymers (glass transition temperature (Tg)) and thus optimize the mechanical properties of the cements (compressive, tensile, shear, etc.) in order to adapt them best to the medical procedure and avoid any post-operative mechanical problems. Introduction of acrylic units such as alkyl acrylates (for example from $C_2$ to $C_{10}$ such as butyl acrylate or ethyl-2-hexyl acrylate) thus allows the Tg of the polymer to be lowered, whereas the presence of more-rigid methacrylate units (isobornyl, tulipaline for example) leads to an increase in Tg of the polymer chain.

Advantageously, the presence of sequences with low Tg in the polymers has the consequence of modifying the mechanical properties of the cements at around body temperature and in particular providing a damping character of the cement with respect to an applied stress (compression, tension, shearing).

In a preferred aspect, with a view to reinforcing the cohesion within the cement obtained from these single-phase formulations, a certain proportion, preferably between 0.1 and 10 mol %, of bifunctional monomers may also be introduced. For example ethylene glycol dimethacrylate will be used, or any other bifunctional monomer polymerizable by a radical mechanism.

The polymers that are dissolve—or suspended—in the liquid monomers may be polymers or copolymers of the random type or block type, in particular PMMA or random copolymers or block copolymers based on MMA and co-monomers such as acrylates, methacrylates or such as non-acrylic monomers (styrene for example). The chains of polymers or of copolymers may have a linear or branched structure or else form particles constituted by an assemblage of chains crosslinked with one another or not crosslinked.

According to an aspect of the invention, the polymers dissolved or suspended in the monomer are selected from those having a low Tg, and having a nature different from that of the monomers. For example, alkyl acrylate polymers may be dissolved in MMA so as to obtain, after polymerization, a composite cement constituted by two types of microdomains, one having a high Tg, the other having a low Tg, which endows the material with damping properties.

According to an alternative, the polymers dissolved or suspended in the monomer may be pretreated thermally at 120° C. for several hours, in particular from 2 to 96 hours, before being introduced into the formulation. This thermal pretreatment makes it possible to decompose the residual initiator contained in the polymers used, and prevent any polymerization during storage in the presence of the mixture of monomers.

The main advantage in using random copolymers consists of being able to modulate the physical and mechanical properties of the cements obtained, as was explained above. An advantage in using branched structures or particles is that formulations are obtained with lower viscosity than in the presence of a linear (co)polymer with the same molecular weight.

In another particular composition of single-phase formulation, the use of copolymers of the block type constituted by incompatible rigid/flexible blocks is another advantageous possibility of the present invention. The use of block copolymers in which at least one block is not compatible with the polymer matrix formed by polymerization of the monomers of the liquid phase also makes it possible to generate microdomains in the matrix that are constituted by an assemblage of immiscible blocks, while the miscible blocks provide cohesion with the matrix. This strategy makes it possible in particular to introduce microdomains constituted by blocks having a low glass transition temperature, for example below 35° C., in particular below body temperature, and therefore relatively flexible, which will reinforce the impact strength and toughness of the implanted cements. The best known example of such "impact" materials based on this strategy is that of "high-impact polystyrene" constituted by microdomains of polybutadiene dispersed in the polystyrene matrix. This morphology makes it possible to absorb impacts and stresses and limit the propagation of fractures in the material.

By way of example, in the case of the single-phase formulations, the flexible blocks having a low Tg may be constituted by various alkyl acrylate units the glass transition temperatures of which vary between +35° C. and −70° C., whereas the block composed of miscible methacrylate units provides cohesion with the matrix, the latter supplying the characteristics of rigidity and stability under compression.

In another single-phase formulation according to the invention, a rather similar result may be obtained from mixtures of PMMA with immiscible polymers or copolymers having a low Tg, below 35° C., in particular below body temperature, in the liquid monomers. By way of example, there may be mentioned as polymers having a low Tg: polyacrylates, polybutadiene, hydrogenated polybutadienes, polyisobutene, amorphous polypropylene etc.

Moreover, while retaining the characteristics of the preceding preparations, the use of dispersions constituted by polymer particles or of particles of copolymers, insoluble in the liquid monomers, makes it possible to obtain formulations of lower viscosity. It may be preferable with these preparations to homogenize the formulation by stirring them before use.

With the aim of reinforcing the cohesion within the cement obtained from these single-phase formulations, reactive functional groups may advantageously be introduced on the polymer chains. By permitting chemical coupling between chains, or even crosslinking of them, these functional groups reinforce the cohesion between the different phases of the material during setting of the cement. The average functionality of these formulations is preferably selected within a range allowing progression of polymerization up to high levels, allowing them to be injected before approaching the gel point, characterized by a large increase in viscosity. For this, the average functionality of these formulations is comprised between 2 and 3 and preferably between 2 and 2.3, which corresponds in the latter case to a gel point above 85% conversion.

One or more radio-opacifying agent(s) and one or more activator(s) of radical polymerization may be added to these monomer/polymer solutions or dispersions. The radio-opacifying agent may be added to the formulation in proportions by weight between 30 and 60 wt % and preferably between 40 and 50 wt %. The radio-opacifying agent may be selected, for example, from barium sulphate or zirconium oxide, introduced in the form of particles. Preferably, the average diameter of said particles is less than 1 mm and preferably less than 1 µm.

The polymerization activator may be selected from the activators of radical polymerization. In the case when the initiator is benzoyl peroxide (BPO), preferably N,N-dimethyl-p-toluidine (DMPT) is used, which facilitates decomposition of the initiator starting from ambient temperature, around 20° C. Other initiator/activator pairs that are usual in this field, such as, for example BPO/Leuco-Crystal Violet, dicumyl peroxide/DMPT may also be used depending on the characteristics required for the polymerization kinetics.

Specific additives may also be added to these single-phase formulations for supplying a characteristic or particular improvement to the formulation or to the final cement. There may be mentioned, by way of non-limitative example, the addition of antibiotic for limiting the risk of post-operative infection.

In some formulations, a radical inhibitor, capable of blocking in particular the action of radicals formed in situ by a thermal or photochemical mechanism, may be added to increase the life of the single-phase formulations. Phenolic derivatives are preferably used in this case, such as hydroquinone (HQ) and in particular derivatives thereof. The latter are added at contents from 0 to 1000 ppm, preferably between 100 and 300 ppm, relative to the total monomers.

According to the invention, the polymer cement is prepared by a method comprising bringing a single-phase formulation as described above into contact with a radical initiator in the form of a thin layer (or film) deposited on a support. Bringing the liquid single-phase formulation into contact with the thin layer (or film) containing the initiator dissolves said initiator and brings it into contact with the activator(s) and the monomer(s) present in said liquid formulation, which initiates polymerization.

Advantageously, said interfacial contacting (passage of the formulation over the coated support) dissolves the film containing the initiator, which on the one hand allows homogeneous distribution of the initiator in the formulation, and on the other hand avoids any waiting by the practitioner at the time of the procedure. This is a major advantage relative to the two-phase solid/liquid formulations, which require a waiting phase corresponding to dissolution of the polymer in the monomer.

The thin layer (or film) containing the initiator may be produced by depositing, on the support, solutions containing the initiator, such as BPO for example, in an organic solvent, which is then removed by evaporation. The solvent is preferably selected from the non-toxic volatile organic compounds, for example acetone or its higher homologues, for example butanone, dimethyl ketone or diethyl ketone. By "thin layer" is meant a layer from about 5 to 500 µm; the thickness of the layer depends on the quantity of initiator required as well as the specific surface area of the support.

Alternatively, the initiator may be dissolved with a film-forming polymer such as, for example, PMMA or a copolymer thereof, so as to obtain, after deposition on the support and evaporation of the solvent, a film of polymer containing the initiator. The characteristics and the proportion of the polymer, such as for example PMMA or a copolymer thereof, make it possible to regulate the quantity of initiator deposited and its dissolution rate in the single-phase formulation.

The invention also relates to a device for injecting a polymer cement for reparative surgery or bone reconstruction, in particular for the fixation of prostheses, for bone repair and for vertebroplasty, comprising
    an injection system with one compartment, such as a single-compartment syringe, containing the liquid single-phase formulation described above,
    an element comprising a support on which a thin layer (or film) containing a polymerization initiator is deposited, such as for example a static mixer or else a support the specific surface area of which is sufficient for depositing thereon a thin layer (or film) containing the initiator.

Such a support may be, for example, a static wing mixer.

This device can be connected, at the time of use, to an injector system allowing direct injection of the prepolymerized formulation, in the course of setting, at the treatment site, in particular in the bone cavity or vertebra, such as a simple tip, a cannula or a trocar, depending on the use envisaged.

The one-compartment injection system containing the liquid single-phase formulation and the element comprising a support on which a thin layer (or film) containing a polymerization initiator is deposited, for example a static mixing system, and, optionally, the injector system, may be packaged separately, in particular within one and the same packaging.

The invention also relates to the use of said device for injecting a polymer cement for reparative surgery or bone reconstruction, in particular for the fixation of prostheses, for bone repair and for vertebroplasty, directly at the treatment site, in particular in the bone cavity or vertebra. This device makes it possible to avoid any manual mixing and any contact of the preparation with the external environment and significantly reduces the corresponding risks. It also allows injection to be performed without a waiting period corresponding to dissolution/dispersion of a first phase in a second phase.

The invention also relates to a method for injecting a polymer cement for reparative surgery or bone reconstruction, said cement being prepared by bringing a liquid single-phase formulation, said formulation comprising a liquid phase containing at least one polymer or copolymer in solution or in suspension in at least one monomer, at least one activator of radical polymerization, and optionally at least one radio-opacifying agent, as described above, into contact with an initiator of radical polymerization deposited in the form of a thin layer or film on a support, as described above.

The invention also relates to a method for injecting a polymer cement for reparative surgery or bone reconstruction, in which a device as described above is used for injecting a polymer cement for reparative surgery or bone reconstruction, in particular for the fixation of prostheses, for bone repair and for vertebroplasty.

The assembly comprising a one-compartment injection system containing the liquid single-phase formulation described above, and an element comprising a support on which the thin layer (or film) containing the initiator (and, optionally, injector system) is deposited, may be stored in a blister pack, away from the light at low temperature, until it is used. Each element of the assembly (one-compartment injection system containing the liquid single-phase formulation, static mixing system comprising a support on which the thin layer (or film) containing the initiator is deposited, and injector) may be packaged separately, with a view to joint use, and said elements can be assembled at the time of injection.

Stored at 20° C. in the dark, the film containing a radical initiator, in particular BPO, may be deposited on the walls of an element of the device, for example a static mixer, in particular a static wing mixer, and can remain active for more than two years.

DETAILED DESCRIPTION OF THE INVENTION

Figure 1A:
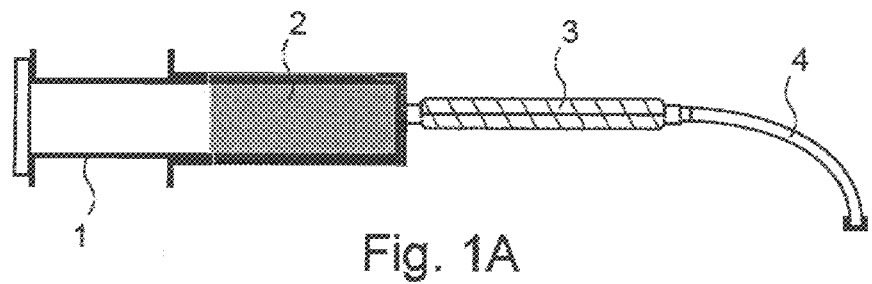
FIGS. 1A, 1B, 1C and 2 show, non-limitatively, devices according to the invention.
Figure 1B:
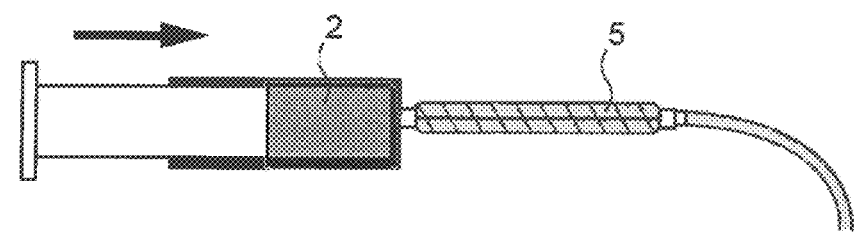
Figure 1C:
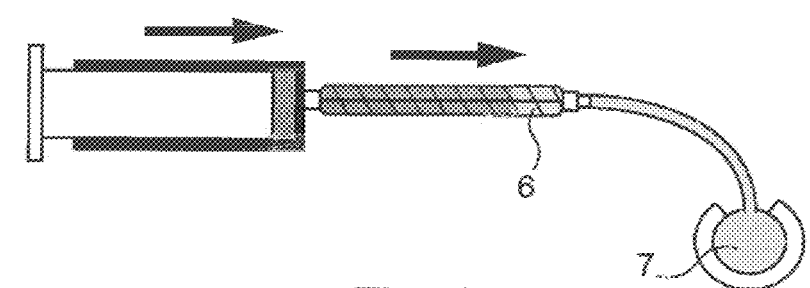

A device according to the invention is shown, by way of non-limitative example, in FIG. 1-A, which shows a single-compartment syringe (1) (in the blocked position) containing a single-phase formulation (2), an element (3) comprising a support on which a film containing the initiator is deposited, said element being connected to a tip (4). Element (3) may be a static mixer. By way of example, FIG. 1-A shows a static wing mixer, said wings being coated with a film of initiator represented by stripes. The static mixer may also be of a different type.

The volume of the single-phase formulation stored in the compartment of the injection system is selected such that it is greater than the volume required (Vreq) for the fixation of the prosthesis or for carrying out bone filling plus the volumes of the element containing the initiator (Vm) and the injector (simple tip, cannula or trocar) (Vi), i.e.:

Volume of single-phase formulation>(Vreq+Vm+Vi),

The prepolymerization of the cement is started during the step of activation/maturation of the single-phase formulations by bringing them into contact with the film containing the initiator deposited on the walls of an element of the device. The film of initiator quickly dissolves in the formulation. The primary initiator radicals are generated rapidly by the action of the activator contained in the single-phase formulations, initiating polymerization starting from ambient temperature. The concentration of initiator as well as the characteristics of the film-forming polymer, typically PMMA or a copolymer thereof, determine the dissolution rate of the initiator as well as the quantity and distribution of radicals within the formulation. Radical polymerization then takes place according to kinetics and with release of heat similar to those of the commercial two-phase or multiphase systems. The maturation/prepolymerization time can be adjusted depending on the proportion of initiator and of activator, after which injection of the prepolymerized system into the bone cavity or into the vertebra may be carried out directly via the connected injector. Final setting of the cement, corresponding to the end of the polymerization step, is accompanied for about 2 to 5 minutes by an exothermic effect of polymerization, leading to maximum temperatures from 70 to 90° C. within the cements and in the biological tissues situated in the immediate proximity, after which the temperature decreases with completion of polymerization. The residual levels of monomer measured in the cements are less than 1 wt %.

The method of activation/polymerization of the liquid single-phase formulations and the manner of injecting them during the surgical procedure are illustrated in FIGS. 1-B and 1-C.

FIG. 1-B shows the step of mixing/activation and of prepolymerization, during which the liquid single-phase formulation is brought into contact with the initiator, which is thus dissolved (5).

FIG. 1-C shows the step of injection, during which the prepolymerized cement (6) is injected into the bone cavity (7).

The invention also relates to a method of injecting polymer cements for reparative surgery or for bone reconstruction, in particular for the fixation of prostheses, for bone repair or for vertebroplasty, said cement being prepared from a liquid single-phase formulation as described above, in which activation of the single-phase formulation is carried out during the injection operation without requiring an operation of manual mixing.

The cements obtained from these single-phase formulations, which are also an object of the invention, have physical properties that can be modulated in relation to their composition and in particular the nature of the monomers and polymers used. The rigidity of the cements can thus be modulated, and more precisely lowered either by copolymerizing the monomer or monomers of the solution or suspension with comonomers of the acrylate type (butyl acrylate, 2-butyl-hexyl acrylate, for example), or by introducing copolymers of the MMA type with acrylates or else with polymers with low Tg. Depending on the composition of the multiphase formu lations, and by comparison with tests carried out with a reference commercial two-phase cement (Biomet®), the Young's modulus (rigidity) of the cements can be lowered by a factor 2 to 10, thus approaching the values of Young's modulus close to bone, and in particular human vertebral cancellous bone.

An alternative for modulating the mechanical properties of the cements obtained from single-phase compositions consists of using polymers or (co)polymers of lower molecular weight or mixtures of polymers or (co)polymers of different molecular weights.

Another way of modulating the characteristics of the cements consists of generating, starting from another single-phase formulation, a material with two-phase morphology by incorporation of a block copolymer having a block with low Tg that is immiscible in the rigid polymer matrix. One of the most suitable copolymers is a block copolymer having a block of MMA or rich in MMA and a block based on acrylate monomers (alkyl acrylates). These cements display mechanical behaviour allowing impacts to be absorbed and propagation of fractures to be limited.

The method for preparing polymer cements from liquid single-phase formulations, as described above, as well as the device and method of application by activation/injection and the cements prepared from these single-phase formulations, according to the invention, provide substantial improvements both in the preparation and under the conditions for long-term storage (3 years) of single-phase formulations for polymer cements for applications in reparative surgery.

The present invention makes it possible in particular to avoid the risks associated with decomposition to potentially initiating radicals, which limit the storage and use over time of these solutions, the viscosity of which increases even when they are stored in a refrigerator (4° C.), as well as those associated with the difficulty of controlling the injection of two solutions having different viscosities using a two-compartment syringe. Moreover, it is much easier for the practitioner to use.

The liquid single-phase formulations according to the invention may be stored in a device comprising a one-compartment injection system and a contacting element comprising a support on which the thin layer (or film) containing the initiator is deposited, to be injected directly into the patient's bone cavity or vertebra. Utilization of the cement, i.e. activation of the single-phase formulation during the injection operation, is carried out under sealed conditions, in the device, without requiring an operation of manual mixing.

Relative to the existing methods, the invention provides novel, simplified solutions in the method of mixing/activation/injection of these single-phase formulations. Moreover, the cements obtained from the liquid single-phase formulations described above have properties under compression, flexure and shear making it possible to reduce the risks of fracture of the treated and/or adjacent parts of bones and vertebrae.

The following examples help to explain the invention concerning the preparation of single-phase formulations and the method of activation/injection thereof as cements for plastic, reparative, or cosmetic surgery. These examples are presented by way of illustration of i) the method for preparing the liquid single-phase formulations, ii) the mechanical characteristics of the cements obtained by the method and iii) applications of the method in the biomedical field, but are in no way exclusive or limitative.

EXAMPLE 1

Preparation of Single-Phase Formulations According to the Invention Containing a Monomer and an Activator (DMPT) as Well as a Polymer and Radio-Opacifying Agent Formulations 1-a) to 1-e) were prepared as described below. The variation of their viscosity was measured over time by rheometry.

Formulation 1-a)

31 g of random copolymer PMMA-MABu (Degalan LP6311, molecular weight 30000 g/mol) is dissolved in 10 g MMA. After dissolution, 22 g of zirconium oxide (Minchen UK DKK Japan) and 0.145 g of N,N-dimethyl para-toluidine are then added under stirring.

Formulation 1-a), once homogenized, is kept in the dark at 20° C. and the variation of its viscosity is measured by rheometry over time. The viscosity changes from 100 Pa·s to 1300 Pa·s after a few weeks.

Formulation 1-b)

200 ppm of hydroquinone is added, as trapping agent of initiating free radicals, to formulation a) and the variation of the viscosity of the formulation over time (stored at 20° C. in the dark) is monitored by rheometer. The viscosity changes from 100 Pa·s to 800 Pa·s after three months.

Formulation 1-c)

In formulation 1-a), PMMA (Degalan LP6311 molecular weight 30 000 g/mol) is treated beforehand at 120° C. for 24 h before being dissolved in MMA. The corresponding formulation c) obtained, once homogenized, is kept in the dark at 20° C. and the variation of its viscosity is measured by rheometry over time. The viscosity changes from 100 Pa·s to 400 Pa·s after one year.

Formulation 1-d)

In formulation 1-a), PMMA (Degalan LP6311, molecular weight 30 000 g/mol) is treated beforehand at 120° C. for 24 h before being dissolved in MMA. 200 ppm of hydroquinone is also added, as free radical trapping agent. Formulation 1-d), once homogenized, is kept in the dark at 20° C. and the variation of its viscosity is measured by rheometry over time. The viscosity changes from 100 Pa·s to 300 Pa·s after 3 years.

Activation and application of the corresponding formulations according to the operating protocol of the invention show that, after different storage times, the polymerization kinetics and the mechanical characteristics of the cements have not undergone any significant change and meet the required criteria.

Formulation 1-e)

PMMA polymer, 14 g (Degalan 6606F, molecular weight 300 000 g/mol) was treated beforehand for 24 h at 120° C. before being dissolved in 42 g of MMA. After dissolution, 44 g of zirconium oxide (Minchen UK DKK Japan), and 100 ppm of a free radical trapping agent, hydroquinone, are then added under stirring. Once homogenized, the formulation is kept in the dark at 20° C.

COMPARATIVE EXAMPLE 2

Solutions Containing the Monomer and the Initiator (Corresponding to the So-Called Multi-Solution Method)

This example illustrates the variation over time, at 20° C., of the viscosity of a solution containing both the monomer (MMA) and the initiator (BPO) as well as a polymer, a radio-opacifying agent and optionally a free radical trapping agent.

The random copolymer PMMA-MABu, 31 g (Degalan LP6311, molecular weight 30 000 g/mol) was treated beforehand for 24 h at 120° C. before being dissolved in 10 g of MMA. After dissolution, 31 g of zirconium oxide (Minchen UK DKK Japan), 0.25 g of benzoyl peroxide (BPO), and 200 ppm of a free radical trapping agent, hydroquinone, are then added under stirring. Once homogenized, the formulation is kept in the dark at 20° C. and the variation of its viscosity is measured by rheometer over time. The viscosity changes from 100 Pa·s to 30000 Pa·s after 7 months.

This example shows that the single-phase formulations according to the invention have advantageous storage properties over time, unlike the "multi-solution" formulations, the viscosity of which increases considerably with the passage of time.

EXAMPLE 3

Preparation of Single-Phase Formulations According to the Invention 3.1 Formulation Based on PMMA and MMA 10 g of polymethyl methacrylate (PMMA, Degalan M825, of molecular weight 80000 g/mol) pretreated at 120° C. is dissolved in 10 g of MMA. The following are then added to the mixture: 16.02 g of zirconium oxide (Minchen UK DKK Japan) of particle size 0.53 μm, 0.145 g of N,N-dimethyl para-toluidine, and finally 200 ppm of hydroquinone. The single-phase formulation has an initial viscosity determined by rheometry of the order of 1000 Pa·s, at 20° C.

3.2 Formulation Based on a Block Copolymer PMMA-b-MABu and MMA 31 g of a poly(methyl methacrylate-block-butyl methacrylate) block copolymer (PMMA-b-MaBu, prepared by controlled radical polymerization, of apparent molecular weight 30000 g/mol) and pretreated at 120° C., is dissolved in 10 g of MMA. The following are then added to the mixture: 22 g of zirconium oxide (Minchen UK DKK Japan) of particle size 0.53 μm, 0.145 g of N,N-dimethyl pare-toluidine, and finally 200 ppm of hydroquinone. The single-phase formulation has an initial viscosity of the order of 100 Pa·s, at 20° C.

EXAMPLE 4

Preparation and Application of Polymer Cements (Activation/Injection)

4.1) Coating of an Element of the Device with a Film of Initiator: Example of a Wing Mixer The internal wings of a static mixer are immersed in a solution of acetone and of purified BPO (50 wt %), in order to coat their surface therewith. The solvent is then removed by evaporation and drying under vacuum, leaving a homogeneous film of BPO on the was of the wings of the mixer. The amount of BPO deposited, determined from the increase in mass of the mixer, can be adjusted by varying the concentration of the solution. The latter typically contain between 30 and 70% of BPO.

An alternative consists of using a solution of acetone and of initiator with a film-forming polymer or copolymer. It is possible for example to use p(MMA-MABu) copolymers with composition similar to that used in the single-phase formulations. Thus, in the case of a solution at 50 wt % of p(MMA-MaBu) copolymer (Degalan LP6311, molecular weight 30 000 g/mol) and of BPO (weight ratio polymer: initiator 1:2) in acetone, the amount of BPO deposited is of the order of 200 mg, an amount that is largely sufficient to obtain rapid polymerization kinetics.

4.2 Activation/Prepolymerization

A device as shown in FIG. 1 is used.

10 cm$^3$ of the single-phase formulation (formulations 1-a) to 1-e) in example 1) contained in the chamber of the syringe (FIG. 1-A) is injected slowly into an element of the device constituted by a static mixer equipped with wings, on the walls of which a film containing 200 mg of initiator has been deposited (FIG. 1-B). During filling of the mixer with the single-phase formulation and bringing it into contact with the film of BPO deposited, the latter is quickly dissolved (2 min) allowing interaction between BPO and N,N-dimethylamino para-toluidine and rapid starting, from ambient temperature, of polymerization of the acrylic monomers. This then develops according to kinetics similar to those observed with the two-phase or multiphase formulations. The maximum of the exothermic effect of polymerization varies from 65 to 35° C., as a function of the proportion of initiator and of activator introduced. This maximum is reached between 10 and 15 min after bringing the formulation into contact with the film of initiator.

Figure 2:
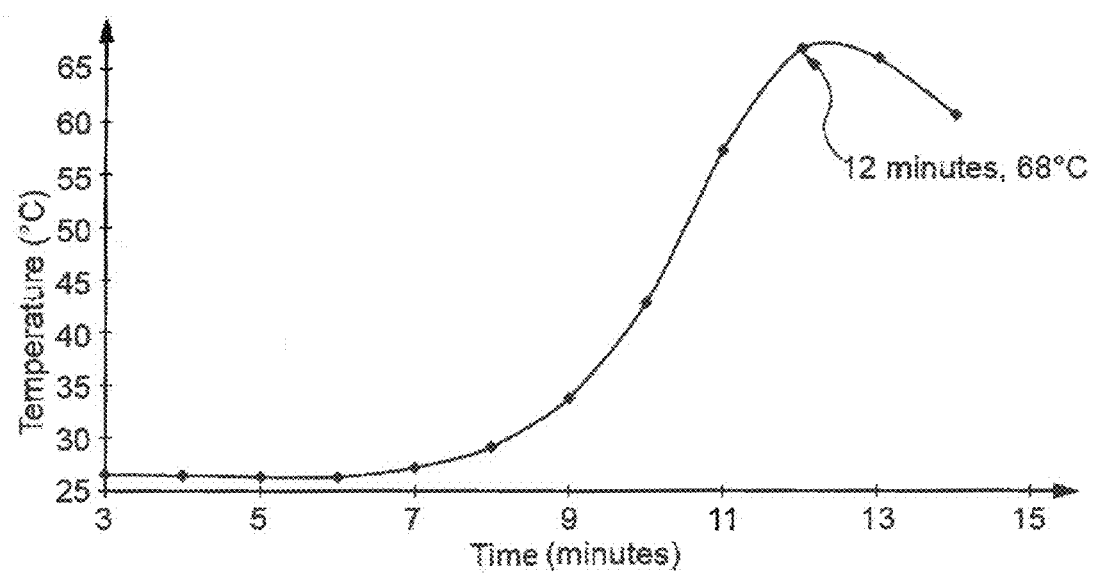

The curve of the increase in temperature as a function of the time observed after injection of formulation 1-b) from example 1 is shown in FIG. 2.

43) Injection

The formulation, activated by passage over the film of polymer containing the initiator, is injected directly by means of a simple tip, a cannula, or a trocar, into the bone cavity where the prosthesis is to be fixed (in the bone or vertebra to be repaired or to be reconstructed).

4.4) Mechanical Properties

The cements obtained with the formulations tested may display either moduli closer to those of human vertebral cancellous bones or moduli equivalent to the moduli of the cements obtained with commercial products.

The mechanical properties of the formulations according to the invention were measured according to standard ISO 5833.

The results are presented in Table 1 below:

TABLE 1

| Formulation used | BPO/PMM A weight ratio | BPO mass deposited (mg) | n | $\sigma_{ave}$ (2% offset) MPa | $E_{ave}$ (MPa) |
|---|---|---|---|---|---|
| Formulations 1-a) to 1-d) of example 1 | 4 | 200 | 20 | 21.9 ± 4.0 | 910 ± 80 |
| Formulation 1-e) of example 1 | 4 | 200 | 6 | 80 ± 5.0 | 1870 ± 352 |
| Human vertebral cancellous bone | Data in the literature | | / | 2.1 ± 1.8 | 187 ± 143 |
| Commercial bone cement (type Biomet Bone Cement V) | Tests performed under identical conditions | | 15 | 72 ± 4.2 | 1665 ± 327 | n = number of tests performed
$\sigma_{ave}$ = average compressive strength
$E_{ave}$ = flexural modulus The results show that the mechanical properties of formulations 1-a) to 1-d) are particularly suitable for vertebroplasty whereas formulation 1-e), which complies with standard ISO5833, can be used without restriction in the field of orthopedic procedures (hip, knee, etc.).

The invention claimed is:

1. A method for preparing polymer cements for reparative surgery or for bone reconstruction, comprising bringing a liquid single-phase formulation, said formulation comprising a liquid phase containing at least one polymer or copolymer in solution or in suspension in at least one monomer, and at least one activator of polymerization, into contact with an initiator of radical polymerization deposited in the form of a thin layer or film on a support.

2. The method according to claim 1, wherein bringing said liquid single-phase formulation into contact with an initiator of radical polymerization deposited in the form of a thin layer or film on a support allows dissolution of said thin layer or film containing the initiator, bringing into contact the initiator and activator of radical polymerization and initiation of polymerization of the monomer or monomers.

3. The method according to claim 1, wherein bringing said liquid single-phase formulation into contact with at least one initiator of radical polymerization is carried out by the passage of said liquid single-phase formulation over an element comprising a support, on which a thin layer or film containing an initiator of radical polymerization is deposited.

4. The method according to claim 1, wherein bringing said liquid single-phase formulation into contact with at least one initiator of radical polymerization takes place in an injection device in which said liquid single-phase formulation is contained in the single reservoir of an injection device equipped at the outlet with an element comprising a support on which a thin layer or a film containing the polymerization initiator is deposited.

5. The method according to claim 1, wherein bringing said liquid single-phase formulation into contact with an initiator of radical polymerization deposited in the form of a thin layer or film on a support takes place at the moment of the surgical procedure.

6. The method according to claim 1, wherein said liquid single-phase formulation contains at least one radio-opacifying agent.

7. The method according to claim 1, wherein the liquid single-phase formulation contains at least one acrylic, monomer, one or more polymers or copolymers, at least one activator of radical polymerization, at least one radio-opacifying agent and at least one additive.

8. The method according to claim 1, wherein the liquid single-phase formulation contains at least one acrylic monomer, or one or more polymers or copolymers, at least one activator of radical polymerization, at least one radio- opacifying agent and at least one additive and wherein said additive is selected from free radical inhibitors and antibiotics.

9. The method according to claim 1, wherein the polymer(s) or the copolymer(s) is/are selected from poly (methyl methacrylate) and random or block copolymer(s) of methyl methacrylate with a monomer having an acrylate or methacrylate structure.

10. The method according to claim 1, wherein the polymer or copolymer chains have a linear, branched or hyper-branched structure, or else form particles constituted by an assemblage of crosslinked or non-crosslinked chains.

11. The method according to claim 1, wherein the polymer or copolymer is of a block polymer or copolymer and has at least one block that is immiscible with the other polymers and copolymers and the immiscible block of which has a glass transition temperature below 35° C.

12. The method according to claim 1, wherein the polymer or copolymer is treated thermally at 120° C. for several hours before being introduced into the formulation.

13. The method according to claim 1, wherein the film deposited on the support and containing the initiator of radical polymerization consists of a mixture of the initiator and of a film-forming polymer or copolymer.

14. The method according to claim 1, wherein it comprises a step of prepolymerization of the single-phase formulation in an element of an injection device comprising a support on which a thin layer or film containing a polymerization initiator is deposited, carried out by activation of the polymerization initiator by the activator contained in the single-phase formulation.

15. A device for injecting a polymer cement for reparative surgery or for bone reconstruction, comprising
a one-compartment injection system containing the liquid single-phase formulation described in claim 1, said liquid single-phase formulation comprising a liquid phase containing at least one polymer or copolymer in solution or in suspension in at least one monomer, and at least one activator of radical polymerization,
an element comprising a support on which a thin layer or a film containing a polymerization initiator is deposited.

16. The device according to claim 15, wherein it is connected to an injector system allowing direct injection of a prepolymerized cement, in the course of setting, at the treatment site.

17. The device according to claim 15, wherein the one-compartment injection system containing the liquid single-phase formulation, an element comprising a support on which a thin layer or a film containing a polymerization initiator is deposited, and, optionally, the injector system, are packaged separately, with a view to joint use.

18. The method according to claim 1, wherein the liquid single-phase formulation contains at least one (meth)acrylic monomer, one or more polymers or copolymers, at least one activator of radical polymerization, at least one radio-opacifying agent and at least one additive.

* * * * *